United States Patent [19]

Bay

[11] Patent Number: 4,727,194
[45] Date of Patent: Feb. 23, 1988

[54] PREPARATION OF A PHOSPHORUS COMPLEX

[75] Inventor: Elliott Bay, Ridgefield, Conn.

[73] Assignee: Stauffer Chemical Company, Westport, Conn.

[21] Appl. No.: 26,311

[22] Filed: Mar. 16, 1987

[51] Int. Cl.$^4$ ................................ C07F 9/02
[52] U.S. Cl. ........................................ 568/16
[58] Field of Search ............................ 568/16

[56] References Cited

U.S. PATENT DOCUMENTS 3,855,310 12/1974 Chopdekar ..................... 568/16
4,634,771 1/1987 Shim et al. ..................... 546/286
4,656,293 4/1987 Kleiner ...................... 568/16 X R

OTHER PUBLICATIONS

Fedorova et al., "Zhur. Obshchei. Khim.", 30, p. 4044 (1960).
Zhmurova et al., "Org. Phos. Comp. Ref.," 705, vol. 3, Monatsh. 70, 1–19 (1937).

Primary Examiner—Paul F. Shaver
Attorney, Agent, or Firm—Hensley M. Flash

[57] ABSTRACT

An improved process for preparing a phosphorus complex of the formula:

$$RP^{\oplus}Cl_3 \cdot P^{\ominus}Cl_6$$

wherein R is selected from the group consisting of: aryl; substituted aryl, wherein the substituent can comprise at least one member selected from the group consisting of nitro, chloro, fluoro, alkyl, fluoro-alkyl, alkoxy and mixtures thereof; alkyl and substituted alkyl by the reaction of phosphorus pentachloride and a phosphonic dichloride of the formula:

$$RPOCl_2$$

wherein R is defined as above, wherein the improvement comprises: reacting the phosphorus pentachloride and the phsophonic dichloride in the presence of an inert solvent capable of co-distilling a phosphorus oxychloride reaction product, for example, chlorobenzene, and co-distilling said phosphorus oxychloride reaction product during the reaction of the phosphorus pentachloride and the phosphonic dichloride. The inert solvent can boil at a temperature ranging from about 120° C. to about 150° C. and the reaction is carried out at a temperature ranging from about 75° C. to about 175° C. A preferred phosphorus complex prepared by this improved reaction scheme is phenyltrichlorophosphonium hexachlorophosphate.

7 Claims, No Drawings

PREPARATION OF A PHOSPHORUS COMPLEX

BACKGROUND OF THE INVENTION

1. Field of the Invention

This invention relates to an improved process for preparing a phosphorus complex and, in particular, phenyltrichlorophosphonium hexachlorophosphate.

2. Related Information

The phosphorus complex of this invention, exemplified by the compound phenyltrichlorophosphonium hexachlorophosphate, is well known in the art and is used in the preparation of various phosphorus-containing compounds.

The article entitled, "Reaction of Phosphorus Pentachloride With Unsaturated Hydrocarbons" by G. K. Fedorova and A. V. Kirsanov, *Zhur. Obshchei. Khim.* 30 4044 (1960), reported the reaction of styrene with phosphorus pentachloride to form a colorless complex with the structure $C_6H_5CH=CHPCl_3^+.PCl_6^-$. This reference further disclosed the reaction of arylphosphonous dichloride with phosphorus pentachloride to form a complex of formula $ArPCl_3^+.PCl_6^-$. These reactions were carried out in benzene at temperatures ranging from about 70° C. to about 80° C. The yield of the complex realized ranged from about 60 weight percent to about 80 weight pecent. However, this reference does not disclose the unique process of this invention, especially because it uses different reagents and does not disclose yields of phosphorus complex in substantially quantitative amounts.

In the article entitled, "Tetrachloro(m-and p-nitrophenyl) Phosphoranes" by I. N. Zhmurova and I. Yu. Voitsekhovskaya, *Org. Phos. Comp. Ref.* 705, Vol. 3, Monatsh. 70 1-19 (1937), the reaction disclosed in the previous reference was cited for preparing the phosphorus complex. It was further stated therein, that m- and p-nitrophenylphosphonic dichlorides required more severe reaction conditions that in the case of arylphosphonic dichlorides which do not contain a nitro group. In particular, it stated that phenyl- and p-tolyl-phosphonic dichlorides react with phosphorus pentachloride in boiling benzene, but m- and p-nitrophenylphosphonic dichlorides react only when heated with phosphorus pentachloride at 150° C. in absence of solvent. This reference further discloses that when nitrophenyl-phosphonic dichloride and phosphorus pentachloride were heated with a condenser set for distillation and a receiver cooled to −80° C. for phosphoryl chloride, the yield realized was only about 65 to about 75 weight percent. It is noted, that in the course of the reaction only a small amount of phosphorus oxychloride was distilled off and the reaction was carried out in the absence of a solvent. The improvements disclosed by the present invention are not disclosed by this reference.

U.S. Pat. No. 4,634,771 issued to Shim et al. Jan. 6, 1987, discloses the reaction of carboxylic acid groups on an aromatic ring compound with a phenylphosphonous dichloride, chlorine, and phosphorus trichloride to convert the carboxylic acid groups to trichloromethyl groups. This reference distinguishes the use of phosphorus pentachloride and suggests that it is specific for the conversion of a carboxylic acid group adjacent, or alpha, to the heteroatom of a N-heteroaromatic (N=nitrogen) compound. This patent further distinguishes the use of phenylphosphonic dichloride and phosphorus pentachloride, citing the disadvantage of requiring the handling of solid phosphorus pentachloride which, due to its sensitivity to moisture, requires special handling conditions. This reference, therefore, effectively distinguishes itself from the invention disclosed herein.

SUMMARY OF THE INVENTION

An object of this invention is to provide a process for preparing a phosphorus complex, exemplified by phenyltrichlorophosphonium hexachlorophosphate, in substantially quantitative yields.

Other objects and advantages of the present invention are described elsewhere within the specification.

This invention is an improved process for preparing a phosphorus complex of the formula:

$$RP^{\oplus}Cl_3.P^{\ominus}Cl_6$$

wherein R is selected from the group consisting of: aryl; substituted aryl, wherein the substituent can comprise at least one member selected from the group consisting of nitro, chloro, fluoro, alkyl, fluoro-alkyl, alkoxy and mixtures thereof; alkyl and substituted alkyl by the reaction of phosphorus pentachloride and a phosphonic dichloride of the formula:

$$RPOCl_2$$

wherein R is defined as above, wherein the improvement comprises: reacting the phosphorus pentachloride and the phosphonic dichloride in the presence of an inert solvent capable of co-distilling a phosphorus oxychloride reaction product and co-distilling said phosphorus oxychloride reaction product during the reaction of the phosphorus pentachloride and the phosphonic dichloride. In this process, a preferred solvent boils at a temperature ranging from about 120° C. to about 150° C. and the preferred phosphorus complex is phenyltrichlorophosphonium hexachlorophosphate.

DETAILED DESCRIPTION OF THE INVENTION

This invention discloses a process for preparing a phosphorus complex of the formula:

$$RP^{\oplus}Cl_3.P^{\ominus}Cl_6.$$

In this complex, R is selected from the group consisting of: $C_6$-$C_{12}$ aryl; $C_6$-$C_{12}$ substituted aryl; $C_1$-$C_6$ alkyl; and $C_1$-$C_6$ substituted alkyl. The substituents on the substituted aryl can comprise at least one member selected from the group consisting of nitro, chloro, fluoro, $C_1$-$C_6$ alkyl, $C_1$-$C_6$ fluoro-alkyl, $C_1$-$C_6$ alkoxy, and mixtures thereof. The substituents on the substituted alkyl can be selected from the group consisting of nitro, chloro, fluoro, and mixtures thereof. A preferred phosphorus complex is when R is phenyl with the resulting complex being phenyltrichlorophosphonium hexachlorophosphate.

It has heretofore been known to prepare the above disclosed phosphorus complex by the reaction of phosphorus pentachloride and a phosphonic dichloride of the formula: $RPOCl_2$, wherein R is defined as above.

This invention discloses an improvement on this heretofore known process. In the process of this invention, the phosphorus pentachloride and the phosphonic dichloride are reacted in the presence of an inert solvent capable of co-distilling a phosphorous oxychloride reaction product. The following equation describes the reaction:

$$RPOCl_2 + 2PCl_5 \xrightarrow{solvent} RP^{\oplus}Cl_3 \cdot P^{\ominus}Cl_6 + POCl_3.$$

The solvent useful in this reaction must be inert to the reactants and, further, must be capable of co-distilling the phosphorus oxychloride reaction product. Suitable solvents can include those solvents that boil at a temperature ranging from about 120° C. to about 150° C. A preferred solvent is chlorobenzene, which boils at 132° C.

It is important in this process that the solvent be used to co-distill the phosphorous oxychloride reaction product during the reaction of the phosphorus pentachloride and the phosphonic dichloride. This is distinct from the usual practice of separating the solvent from the reaction products after the reaction is completed or, in the alternative, carrying out the reaction under reflux conditions.

The primary reaction between the phosphorus pentachloride and the phosphonic dichloride can be carried out at a temperature ranging from about 75° C. to about 175° C. with a temperature ranging from about 120° C. to about 135° C. being preferred.

The molar ratio of the reactions, i.e., phosphorus pentachloride to phosphonic dichloride can range from about 0.1:1 to about 10:1. However, the stoichiometric ratio of 2:1 is preferred for economic reasons. The reaction can be carried out at atmospheric pressure.

As heretofore practiced, the reaction between the phosphorus pentachloride and the phosphonic dichloride was carried out with or without a solvent and especially without the careful selection of a particular solvent. Additionally, the concurrent distillation of the resulting phosphorus oxychloride reaction product was neither disclosed nor suggested. The improvement resulting from following the additional steps of the process of this invention includes, the preparation of the resulting phosphorus complex in substantially quantitative yield. This is compared to the prior known process wherein the yields usually realized range from about 60 to about 75 weight percent. In this process, the yields should range from above 80 weight percent to a substantially quantitative yield.

The following experiment describes various embodiments of this invention. Other embodiments will be apparent to one of ordinary skill in the art from a consideration of the specification or practice of the invention disclosed herein. It is intended that the specification and experiment be considered as exemplary only, with the true scope and spirit of the invention being indicated by the claims which follow the experiment.

EXPERIMENT

A solution of chlorobenzene (150 ml) and phosphorus trichloride (73 g, 0.532 mole) was placed in a 500 ml four-necked flask under a nitrogen atmosphere. The flask was fitted with an overhead stirrer, reflux condenser, thermometer, and gas inlet tube. Chlorine gas (38 g, 0.535 mole) was blown onto the surface of the stirred solution at a rate of 1 g/min. The reaction temperature increased to 70° C. as the chlorine reacted with the phosphorus trichloride to prepare phosphorus pentachloride. The gas inlet tube was replaced with an addition funnel after the chlorine addition was completed.

Phenylphosphonic dichloride (50 g, 0.256 mole) was added through the addition funnel over a 10-minute period to the stirred slurry of phosphorus pentachloride at 70° C. The reaction mixture was heated to 120° C. for two hours. The reflux condenser was replaced with a distilling head and the reaction heated to boiling (~132° C.) for about two hours. During this two-hour time period, the reaction by-product, phosphorus oxychloride, and about half of the solvent were co-distilled. The reaction mixture was then cooled to room temperature. The reaction flask was stoppered and placed in a nitrogen-filled glove box. The reaction mixture was filtered through a sintered glass funnel in the glove box. The solid product was placed in a vacuum dessicator and the last traces of solvent removed under vacuum at room temperature. The dry weight of the resulting phenyltrichlorophosphonium hexachlorophosphate was 106 g, representing a yield of 90 weight percent.

What is claimed is:

1. An improved process for preparing a phosphorus complex of the formula:

$$RP^{\oplus}Cl_3 \cdot P^{\ominus}Cl_6$$

wherein R is selected from the group consisting of: aryl; substituted aryl, wherein the substituent can comprise at least one member selected from the group consisting of nitro, chloro, fluoro, alkyl, fluoro-alkyl, alkoxy and mixtures thereof; alkyl and substituted alkyl by the reaction of phosphorus pentachloride and a phosphonic dichloride of the formula:

$$RPOCl_2$$

wherein R is defined as above, wherein the improvement comprises: reacting the phosphorus pentachloride and the phosphonic dichloride in the presence of an inert solvent capable of co-distilling a phosphorus oxychloride reaction product and co-distilling said phosphorus oxychloride reaction product during the reaction of the phosphorus pentachloride and the phosphonic dichloride.

2. The process of claim 1 wherein the solvent boils at a temperature ranging from about 120° C. to about 150° C.

3. The process of claim 1 wherein the solvent is chlorobenzene.

4. The process of claim 1 wherein the reaction is carried out at a temperature ranging from about 75° C. to about 175° C.

5. The process of claim 1 wherein the molar ratio of phosphorus pentachloride to phosphonic dichloride ranges from about 0.1:1 to about 10:1.

6. The process of claim 1 wherein R is phenyl.

7. The process of claim 6 wherein the solvent is chlorobenzene, the reaction is carried out at a temperature ranging from about 120° C. to about 135° C., and the molar ratio of phosphorus pentachloride to phosphonic dichloride is 2:1.

* * * * *